US012527897B2

(12) United States Patent
Ochiai et al.

(10) Patent No.: US 12,527,897 B2
(45) Date of Patent: Jan. 20, 2026

(54) MILKING MACHINE

(71) Applicant: Pigeon Corporation, Chuo-ku (JP)

(72) Inventors: Yukifumi Ochiai, Tokyo (JP); Yoshihiro Shimomura, Chiba (JP); Yuina Ando, Chiba (JP); Hyunjin Im, Chiba (JP); Hayato Ueno, Chiba (JP); Tsukasa Hattori, Chiba (JP)

(73) Assignee: Pigeon Corporation, Tokyo (JP)

(*) Notice: Subject to any disclaimer, the term of this patent is extended or adjusted under 35 U.S.C. 154(b) by 926 days.

(21) Appl. No.: 17/775,813

(22) PCT Filed: Nov. 14, 2019

(86) PCT No.: PCT/JP2019/044682
§ 371 (c)(1),
(2) Date: May 10, 2022

(87) PCT Pub. No.: WO2021/095199
PCT Pub. Date: May 20, 2021

(65) Prior Publication Data

US 2022/0339331 A1 Oct. 27, 2022

(51) Int. Cl.
*A61M 1/06* (2006.01)

(52) U.S. Cl.
CPC .................................. *A61M 1/064* (2014.02)

(58) Field of Classification Search
CPC .. A61M 1/064; A61M 2205/071; A61M 1/06; A61M 1/68; A61M 1/82; F04B 9/14
See application file for complete search history.

(56) References Cited

U.S. PATENT DOCUMENTS

2003/0204164 A1* 10/2003 Britto .................... A61M 1/064 604/74
2006/0276745 A1* 12/2006 Tsai ........................ A61M 1/81 604/74

(Continued)

FOREIGN PATENT DOCUMENTS

CN 110478544 A * 11/2019 ............ A61M 1/062
JP 2019-10350 A 1/2019

OTHER PUBLICATIONS

"European Application Serial No. 19952257.4, European Search Report dated Jun. 28, 2023", (Jun. 28, 2023), 7 pgs.

(Continued)

*Primary Examiner* — Chelsea E Stinson
*Assistant Examiner* — Lei Nmn Gonzalez
(74) *Attorney, Agent, or Firm* — Schwegman Lundberg & Woessner, P.A.

(57) ABSTRACT

A breast pump includes a body including a hood attachment portion, a bottle attachment portion, and an inner passage extending between the hood attachment portion and the bottle attachment portion; a diaphragm configured to generate negative pressure in the inner passage; a handle manually operated to move back and forth; and a link mechanism configured to support the handle in a manner movable back and forth relative to the body. The handle is configured to change pressure of the inner passage from a normal state to a negative state by displacing the diaphragm in a lifting direction. The link mechanism is configured to apply an operation force to the handle that becomes maximal during handle movement when the handle is moved in an operation direction that changes the pressure from the normal state to the negative state.

18 Claims, 5 Drawing Sheets

(56) References Cited

U.S. PATENT DOCUMENTS

| | | | |
|---|---|---|---|
| 2015/0335800 | A1 | 11/2015 | Yamashita |
| 2019/0143014 | A1 | 5/2019 | Ochiai |
| 2020/0171223 | A1 | 6/2020 | Ochiai et al. |

OTHER PUBLICATIONS

International Application No. PCT/JP2019/044682, Search Report mailed Apr. 2, 2020 (English translation), 2 pgs.

* cited by examiner

MILKING MACHINE

This application is a U.S. National Stage Filing under 35 U.S.C. 371 from International Application No. PCT/JP2019/044682, filed on Nov. 14, 2019, and published as WO 2021/095199 A1 on May 20, 2021, which is incorporated by reference herein in its entirety.

TECHNICAL FIELD

The present disclosure relates to a breast pump for manually extracting breast milk.

BACKGROUND ART

Patent Document 1 discloses a breast pump including a body, attached to a hood that is fitted to a breast and to a bottle that stores breast milk, and a manual handle, pivotably attached to the body. The body includes an inner passage, connecting a milking port and the bottle, and a diaphragm that causes the pressure of the inner passage to become negative. The handle is pivotably supported by the upper portion of the body and extends downward toward the bottle. The hood is fitted to the breast, with four of the fingers excluding the thumb placed on the handle, and the thumb is placed on the body. Then, the handle is pivoted toward the body. The pivotal movement of the handle deforms and lifts the diaphragm to generate negative pressure in the inner passage so that breast milk extracted from a nipple flows into the inner passage.

The operation force of the handle gradually increases until the handle reaches its maximum pivotal position. When the handle has been pivoted to the maximum pivotal position, the operation force is the maximum, the lifted diaphragm is at the highest position, and the negative pressure is the maximum.

CITATION LIST

Patent Literature

Patent Literature 1: Japanese Laid-Open Patent Publication No. 2019-10350

SUMMARY OF INVENTION

Technical Problem

A breast pump may be used to stimulate the nipple and breast by continuing the state of negative pressure for a predetermined period. When used in such a manner, the pivoted handle is continuously held near or at the maximum pivotal position in the pivotal operation direction for a predetermined period. Thus, the operation force of the handle remains maximal or close to maximal. This results in a tendency for increasing the muscle load on the hand and forearm of the user.

It is an objective of the present disclosure to provide a breast pump that reduces the muscle load on the hand or forearm of a user.

Solution to Problem

A breast pump that achieves the above objective includes: a body including a hood attachment portion to which a hood that is configured to be fitted to a breast and includes a milking port is attached, a bottle attachment portion to which a bottle that stores breast milk is attached, and an inner passage extending between the hood attachment portion and the bottle attachment portion; a diaphragm configured to generate negative pressure in the inner passage; a handle manually operated to move back and forth, the handle being configured to change pressure of the inner passage from a normal state to a negative state by displacing the diaphragm in a lifting direction; and a link mechanism configured to support the handle in a manner movable back and forth relative to the body. The link mechanism is configured to apply an operation force to the handle that becomes maximal during handle movement when the handle is moved in an operation direction that changes the pressure from the normal state to the negative state. The above configuration reduces an operation force when the handle is moved to the maximum movement position or to a location near the maximum movement position. This reduces the muscle load on the hand or arm of a user.

In the above breast pump, the link mechanism may include a link member located between the handle and the body, the link member including a proximal end configured to be pivoted relative to the handle and a distal end configured to be pivoted relative to the body. In this case, the link mechanism may be configured so that when the handle is moved in the operation direction, a first pivotal fulcrum between the link member and the handle moves toward a straight line that connects a second pivotal fulcrum, between the link member and the body, and a point of action, at which the handle lifts the diaphragm. With the above configuration, a toggle mechanism is implemented by a simple configuration where the link member is arranged between the body and the handle.

In the above breast pump, the link mechanism may further include a support member attached to the body in a manner rotatable in a circumferential direction. In this case, the link member may be attached to the body by the support member, and the handle may be rotatable about the point of action in the circumferential direction of the body. With the above configuration, the handle may be rotatable about the point of action relative to the diaphragm and about the body in the circumferential direction when supported by the support member. The user can position the handle to allow for easy operation.

In the above breast pump, the link member includes two arms each including a distal end connected to the support member, and a connection portion connecting proximal ends of the two arms. The handle includes a lever, an attachment extending from a distal end of the lever and connected to the diaphragm to lift the diaphragm, and two link pieces extending from the lever and connected to the proximal ends of the two arms. The first pivotal fulcrum is a pin arranged on one of the arm and the link piece and engaged with a pin hole arranged in the other one of the arm and the link piece. The second pivotal fulcrum is a support pin arranged on one of the arm and the support member and engaged with a bearing arranged on the other one of the arm and the support member. With the above configuration, a toggle mechanism is implemented by a simple configuration.

The above breast pump may further include an inserted portion inserted into the inner passage. With the above configuration, even when enlarging the inner passage to facilitate cleaning, the inserted portion will still be inserted into the enlarged portion of the inner passage. This limits increases in the volume of the inner passage and minimizes decreases in the milk extracting efficiency.

The above beast pump may further include an inserted portion inserted into the inner passage. In this case, the inner passage may include a negative pressure generating path closed by the diaphragm, the negative pressure generating path being arranged such that a central axis of the negative pressure generating path coincides with a bottle axis that extends parallel to a central axis of the bottle extending in a height direction of the bottle. In this case, the inserted portion may be inserted into the negative pressure generating path, and the second pivotal fulcrum and the point of action may be located on the bottle axis. With above configuration, the diaphragm is lifted such that the inserted portion is moved along the negative pressure generating path.

Advantageous Effects of Invention

The present invention reduces the muscle load on the hand or arm of a user.

DESCRIPTION OF EMBODIMENTS

A breast pump will now be described with reference to FIGS. 1 to 7.

Figure 1:
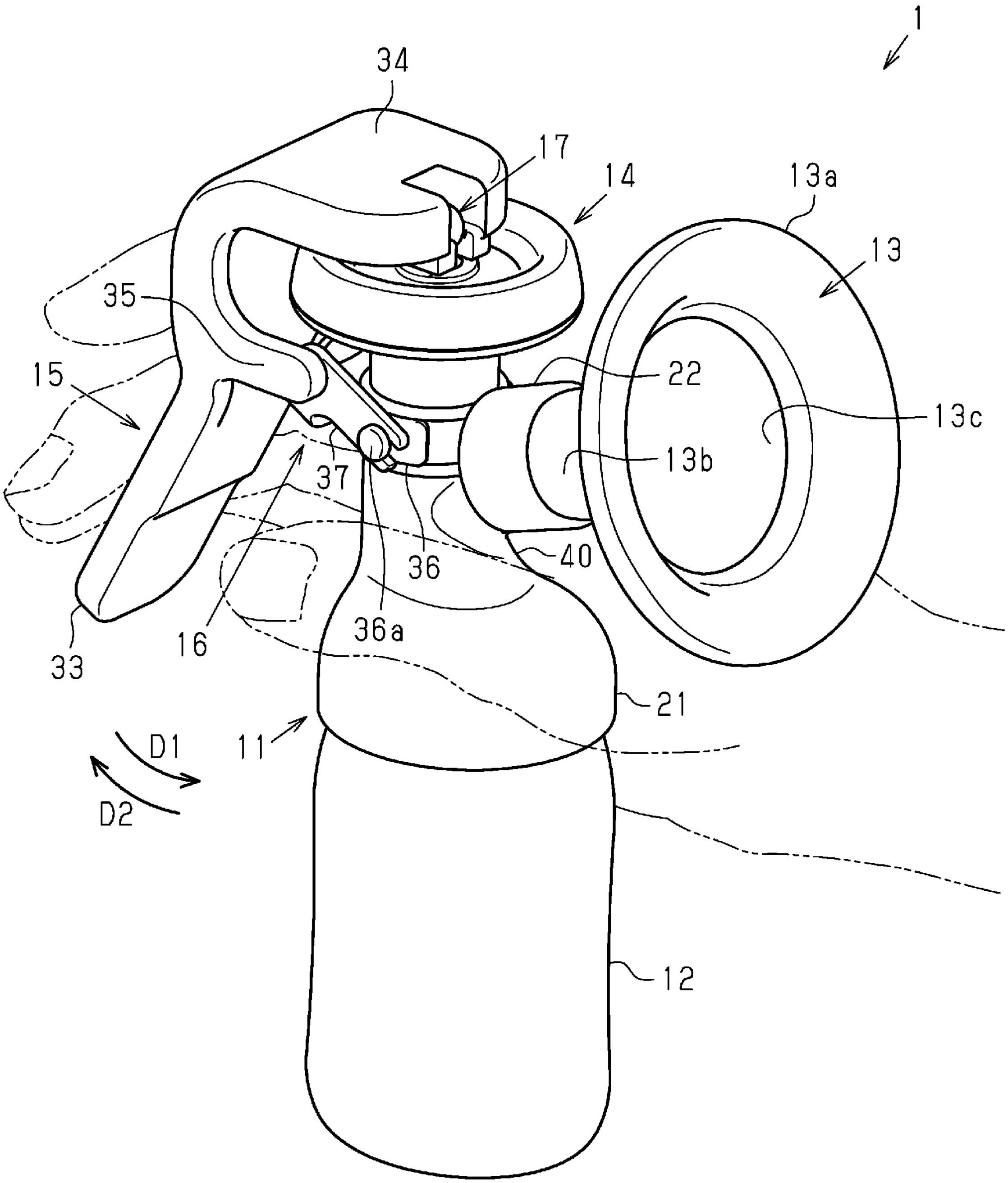
FIG. 1 is a perspective view of a breast pump.

As shown in FIG. 1, a breast pump 1 is sized to allow for manual operation by a user using one hand. The breast pump 1 includes a body 11, a bottle 12, a hood 13, a diaphragm 14, a handle 15, a link mechanism 16, and a lifting member 17.

The body 11 is connected to the bottle 12 that stores breast milk and the hood 13 that is fitted to a breast. The body 11 is a molded product made of a synthetic resin material that is lightweight and hard. Specifically, the body 11 is formed from a synthetic resin material such as polypropylene, polycarbonate, polycycloolefin, polyethersulfone, polyphenylsulfone, or the like.

Figure 2:
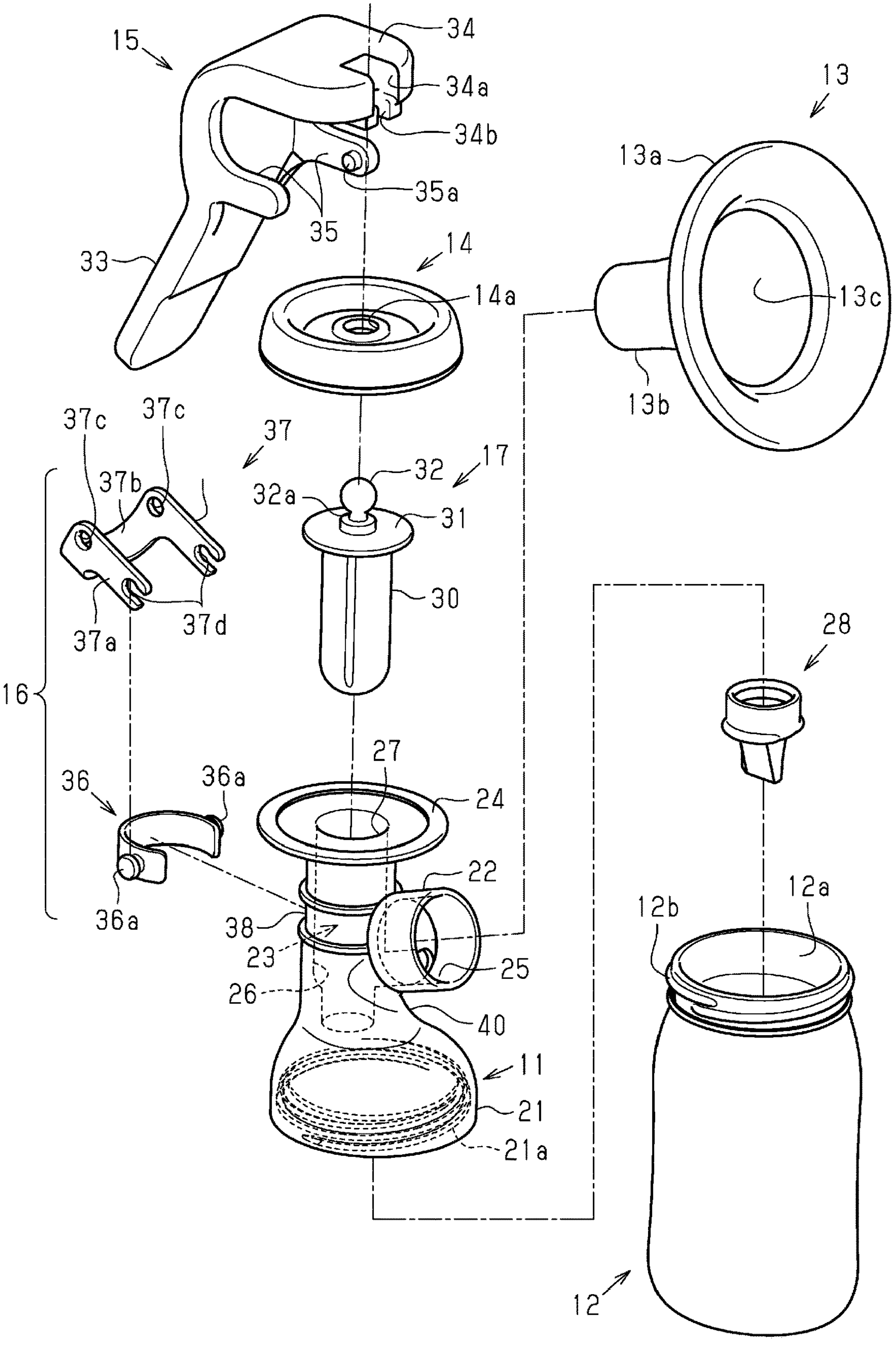
FIG. 2 is an exploded perspective view of the breast pump of FIG. 1.

As shown in FIG. 2, the body 11 includes a bottle attachment portion 21, a hood attachment portion 22, and an inner passage 23. The bottle attachment portion 21 is located downward from the hood attachment portion 22. The bottle 12 is a container that stores breast milk and includes a bottle opening portion 12*a* connected to the bottle attachment portion 21. In the bottle opening portion 12*a*, the outer surface of the circumferential wall forming an opening includes a male thread 12*b*. When an artificial nipple is attached to the bottle opening portion 12*a* instead of the body 11, the bottle 12 can be used as a feeding bottle. The inner side of the bottle attachment portion 21 includes a recess into which the bottle opening portion 12*a* can be threaded, and the inner surface of the bottle attachment portion 21 forming the recess includes a female thread 21*a* threaded with the male thread 12*b*.

The hood attachment portion 22 is tubular. The hood 13, which is dome-shaped or horn-shaped in correspondence with the shape of the breast, includes an increased diameter portion 13*a* fitted to the breast and a tubular portion 13*b* arranged at the top of the increased diameter portion 13*a*. The inner side of the increased diameter portion 13*a* forms a milking port 13*c*. An elastic pad or the like is attached to the rim, or open end, of the increased diameter portion 13*a* so that the increased diameter portion 13*a* can be tightly fitted to the breast. The tubular portion 13*b*, which is tubular, is inserted and fitted into the hood attachment portion 22.

Figure 3:
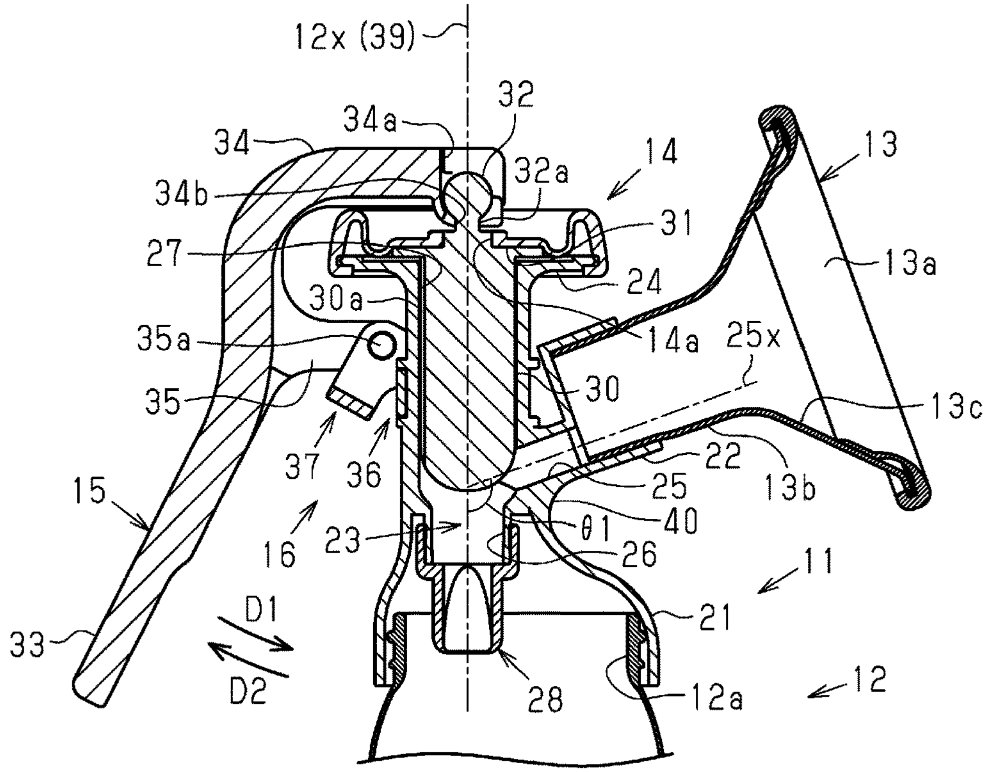
FIG. 3 is a cross-sectional view showing an inner passage of the breast pump of FIG. 1 in a normal pressure state.

As shown in FIG. 3, the inner passage 23 inside the body 11 extends between and connects the bottle attachment portion 21 and the hood attachment portion 22. The inner passage 23 also extends among and connects the bottle attachment portion 21, the hood attachment portion 22, and an attachment end 24 to which the diaphragm 14 is attached. The inner passage 23 includes an inlet path 25, a temporary reservoir 26, and a negative pressure generating path 27.

The inlet path 25, which connects the hood attachment portion 22 and the temporary reservoir 26, extends downward to the temporary reservoir 26 and is located at the inner side of the hood attachment portion 22. The temporary reservoir 26, which is an open space used to temporarily store breast milk received from the inlet path 25 when negative pressure is generated, extends downward and is located at the inner side of the bottle attachment portion 21. For example, the temporary reservoir 26 is aligned with a bottle axis 12*x* that extends parallel to the central axis of the bottle 12 extending in the height direction (vertical direction) of the bottle 12 attached to the bottle attachment portion 21. In one example, the center line of the temporary reservoir 26 coincides with the bottle axis 12*x*. The lower end of the temporary reservoir 26 faces the bottle opening portion 12*a* when the bottle 12 is attached to the bottle attachment portion 21. The angle of the inlet path 25 with respect to the temporary reservoir 26, specifically, angle $\theta 1$ of a center line 25*x* of the inlet path 25 with respect to the bottle axis 12*x* extending through the temporary reservoir 26 is set to, for example, 90° to 180°, preferably, 90° to 135°.

A valve member 28 is attached to the lower end of the temporary reservoir 26 and located at the bottle opening portion 12*a*. The valve member 28 is a check valve including, for example, a duckbill valve. The valve member 28 checks the reverse flow of the breast milk or air inside the bottle 12 back toward the body 11 and partitions the inner passage 23 and the internal space of the bottle 12 so that the pressure of the inner passage 23 becomes negative. The valve member 28 is formed from natural rubber or a synthetic resin material having flexibility, elasticity, and the like such as silicone rubber, and/or elastomer.

The valve member 28 includes two flexible flaps. A slit is formed between the flaps. When the inner passage 23 is in a negative pressure state, the flaps of the valve member 28 contact each other and close the slit. This closes the lower end of the temporary reservoir 26 and temporarily stores the breast milk from the inlet path 25. When the pressure of the inner passage 23 returns to normal, the flaps are separated to open the slit. This connects the temporary reservoir 26 and the inside of the bottle 12, and the breast milk stored in the temporary reservoir 26 flows into the bottle 12.

The negative pressure generating path 27 branches from the temporary reservoir 26 separately from the inlet path 25. Specifically, the negative pressure generating path 27 extends upward from the upper end of the temporary reservoir 26 or the outlet of the inlet path 25, which extends toward the temporary reservoir 26. The negative pressure generating path 27 is larger than the inlet path 25 in diameter and is also larger than the temporary reservoir 26 in diameter. The negative pressure generating path 27 has a diameter that allows, for example, a user to insert a finger into the negative pressure generating path 27. The negative pressure generating path 27 is aligned with the bottle axis 12*x* in the same manner as the temporary reservoir 26. In one example, the center line of the negative pressure generating path 27 coincides with the bottle axis 12*x*.

The upper end of the negative pressure generating path 27 defines the attachment end 24 to which the diaphragm 14 is attached. The attachment end 24 extends outward to form a flange and increase the area of the opening. The attachment end 24 is covered by the diaphragm 14.

The diaphragm 14 generates negative pressure in the inner passage 23. The diaphragm 14 is formed from natural rubber or a synthetic resin material having flexibility, elasticity, and the like such as silicone rubber and/or elastomer. The diaphragm 14 is engaged with the attachment end 24 to close the attachment end 24. The inner passage 23 includes three ends, specifically, the end of the inlet path 25 where the hood 13 is attached, the lower end of the temporary reservoir 26 where the valve member 28 is attached, and the attachment end 24. When the hood 13 is fitted to the breast and the milking port 13*c* is closed, that is, when the end of the inlet path 25 is closed, the remaining ends of the inner passage 23, specifically, the lower end of the temporary reservoir 26 and the attachment end 24 are closed by the valve member 28 and the diaphragm 14 so that the inner passage 23 becomes a substantially sealed space. The lifting member 17 serving as a connector that is connected to the handle 15 is arranged at the inner side of the diaphragm 14.

The lifting member 17 is a molded product formed from a synthetic resin material that is harder than the diaphragm 14 such as polycarbonate, polycycloolefin, polyethersulfone, polyphenylsulfone, or the like. The lifting member 17 is a portion connected to the handle 15 and includes a plate 31, a connection projection 32, and an inserted portion 30.

The plate 31 is arranged on the inner surface of the diaphragm 14. The connection projection 32 projects from the central portion of the surface of the plate 31 that faces the diaphragm 14. The diaphragm 14 includes a through-hole 14*a* extending through the central portion of the diaphragm 14, and the connection projection 32 projects upward from the diaphragm 14 through the through-hole 14*a*. The connection projection 32 includes a spherical distal end, and an engagement groove 32*a* at the bottom end of the sphere.

The inserted portion 30, which is inserted into the negative pressure generating path 27, is arranged on the plate 31. The inserted portion 30 is cylindrical and projects from the plate 31. The inserted portion 30 reduces the volume of the negative pressure generating path 27. The inserted portion 30 has a diameter set to form a gap 30*a* between the outer surface of the inserted portion 30 and the inner surface of the negative pressure generating path 27. The inserted portion 30 is a projection projecting from the plate 31 and inserted into the negative pressure generating path 27 that forms an internal space. The projection of the inserted portion 30 is shaped in conformance with the inner shape of the negative pressure generating path 27 into which the inserted portion 30 is inserted. In one example, the inserted portion 30 is a projection having the form of a cylinder or a tube having a closed end. In one example, the negative pressure generating path 27 is shaped as a hollow tube having an internal space.

The inserted portion 30 has an outer diameter that is smaller than the inner diameter of the negative pressure generating path 27.

The gap 30*a* formed when the inserted portion 30 is inserted into the negative pressure generating path 27 allows the inserted portion 30 to move smoothly in the vertical direction even when the inserted portion 30 is inclined relative to the negative pressure generating path 27. Further, the inserted portion 30 has a length set such that the inserted portion 30 does not close the outlet of the inlet path 25 connected to the temporary reservoir 26 when the diaphragm 14 is lifted. Thus, the inserted portion 30 allows breast milk to flow into the temporary reservoir 26 from the inlet path 25 when negative pressure is generated. Further, the length of the inserted portion 30 is set such that the inserted portion 30 is located at the outlet of the inlet path 25 or at the upper end of the temporary reservoir 26 when the diaphragm 14 is not deformed.

The link mechanism 16 pivotably supports the handle 15 on the body 11. The handle 15 is formed from a synthetic resin material such as polypropylene, polycarbonate, polycycloolefin, polyethersulfone, polyphenylsulfone, or the like. The handle 15 includes a lever 33 and an attachment 34 and is L-shaped in its entirety. The lever 33 is a piece that serves as a handle and extends downward toward where the bottle 12 is located. The outer surface of the handle 15 is curved to allow for easy handling and held by the user with fingers other than the thumb. The lever 33 is curved gradually outward.

The attachment 34 is a piece that extends above the diaphragm 14. The attachment 34 lifts the diaphragm 14 with the lifting member 17 and includes a recess 34*a*. The bottom surface of the recess 34*a* includes an engagement hole 34*b*. The connection projection 32 of the lifting member 17 is inserted into the engagement hole 34*b* so that the engagement hole 34*b* is engaged with the engagement groove 32*a*, and the position where the engagement hole 34*b* is engaged with the connection projection 32 is the point of action for the diaphragm 14. The connection projection 32 is aligned with the bottle axis 12*x*. Accordingly, the handle 15 is connected to the diaphragm 14 by the lifting member 17 and can lift the diaphragm 14 with the lifting member 17 along the bottle axis 12*x*. This allows the gap 30*a* between the inner surface of the negative pressure generating path 27 and the inserted portion 30 to be reduced so that the volume of the inner passage 23 does not increase. The handle 15 is rotatable about the connection projection 32.

The handle 15 includes two link pieces 35 that are connected to the link mechanism 16 near the boundary between the lever 33 and the attachment 34. Each of the link pieces 35 extends from the lever 33 substantially parallel to the attachment 34 and includes a handle pin 35*a* serving as a first pivotal fulcrum at its distal end.

The link mechanism 16 includes a support member 36 and a link member 37. The support member 36 is attached to the base of the attachment end 24 in a manner rotatable in the circumferential direction. The support member 36 is rotated about the base of the attachment end 24 within a range excluding where the hood 13 is located.

The support member 36 is C-shaped. The base of the attachment end 24 is tubular and includes a grooved guide portion 38 extending in the circumferential direction. The support member 36 is fitted onto the guide portion 38 so as to be rotatable in the circumferential direction. The outer surface of the support member 36 near each end includes a support pin 36*a* serving as a second pivotal fulcrum. The support pins 36*a* are aligned with the bottle axis 12*x* in side view.

The link member 37 includes two arms 37*a* and a connection portion 37*b* that connects the two arms 37*a*. The proximal end of each arm 37*a* includes a pin hole 37*c* engaged with the corresponding one of the handle pins 35*a*. The distal end of each arm 37*a* includes a bifurcated bearing 37*d*. The support pins 36*a* are engaged with the bearings 37*d*. The connection portion 37*b* extends between the pin holes 37*c* of the two arms 37*a* to connect the proximal ends of the two arms 37*a*. The connection portion 37*b* is curved so as not to interfere with the base of the attachment end 24 of the body 11. When the handle 15 is not operated, a straight line 39 that connects the point of action, which is where the connection projection 32 is engaged with the engagement hole 34*b*, to the support pins 36*a*, which is the second pivotal fulcrum, coincides with the bottle axis 12*x* in side view. When the handle 15 is operated in the direction of arrow D1, the handle pins 35*a*, which define the first pivotal fulcrum, moves toward the straight line 39. The handle pins 35*a* are moved to positions that overlap the straight line 39 when the handle 15 is at the maximum operation position.

As described above, the link mechanism 16 includes the support member 36 and the link member 37 so that the handle 15 and the link mechanism 16 form a toggle mechanism between the point of action, the first pivotal fulcrum, and the second pivotal fulcrum. Thus, when the user operates the handle 15 in the direction of arrow D1, the operation force gradually increases until the handle 15 moves beyond a given position in the operation range. The operation force becomes the greatest at the given position and gradually decreases beyond the given position.

The body 11 includes a neck 40 at the lower side of the hood attachment portion 22, which is opposed to the handle 15. The user engages the base of the thumb with the neck 40. Specifically, the user holds the breast pump 1 in a palm by placing the fingers other than the thumb on the lever 33 and engaging the neck 40 with the base of the thumb to move and operate the handle 15 with the link mechanism 16.

The operation of the breast pump 1 will now be described.

Figure 4:
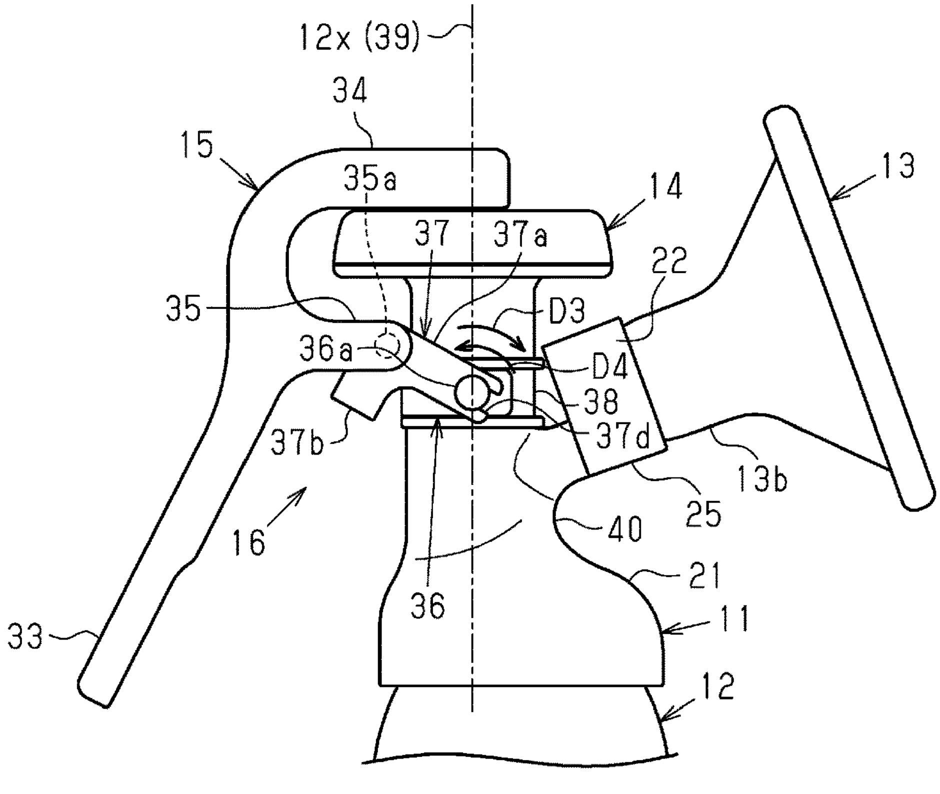
FIG. 4 is a side view showing a link mechanism when the inner passage of the breast pump of FIG. 1 is in the normal pressure state.

When extracting breast milk, the user holds the breast pump 1 by placing the fingers other than the thumb on the handle 15 and engaging the neck 40 of the body 11 with the base of the thumb and fits the hood 13 to the breast of the user to close the milking port 13*c*. Thus, the inner passage 23 becomes a substantially sealed space. Further, the user rotates the handle 15 about the connection projection 32 relative to the body 11 with the support member 36 guided by the guide portion 38 to facilitate handle operation by conforming to individual differences such as the physique of the user. In this case, as shown in FIG. 4, the connection portion 37*b* of the link member 37 is pivoted about the support pins 36*a* away from the body 11 in the direction of arrow D4.

Figure 5:
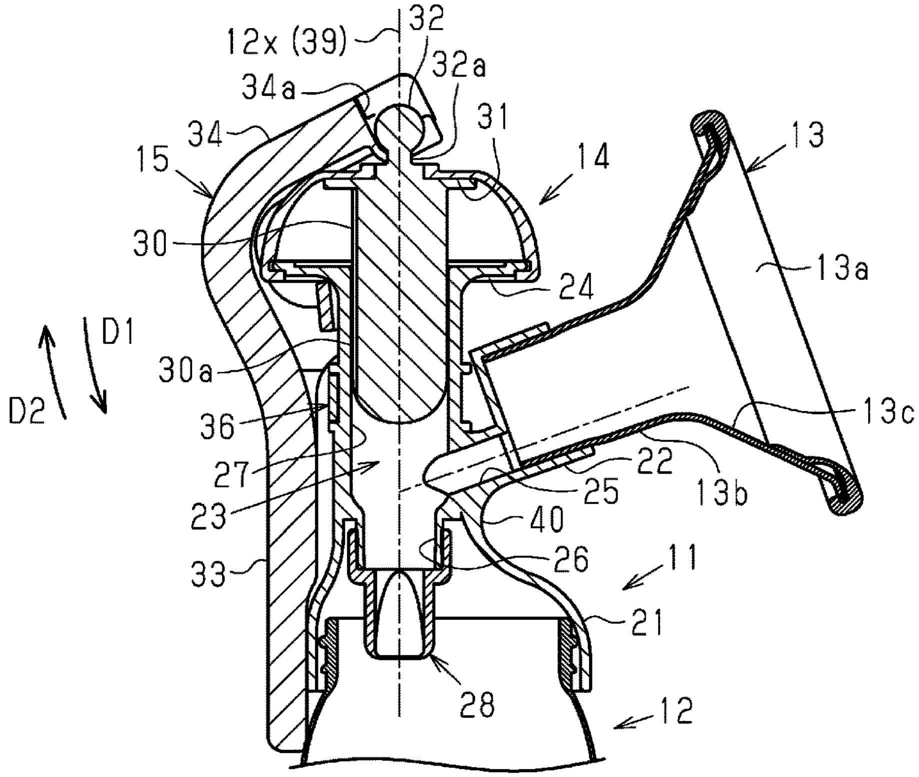
FIG. 5 is a cross-sectional view showing the inner passage of the breast pump of FIG. 1 in a negative pressure state.
Figure 6:
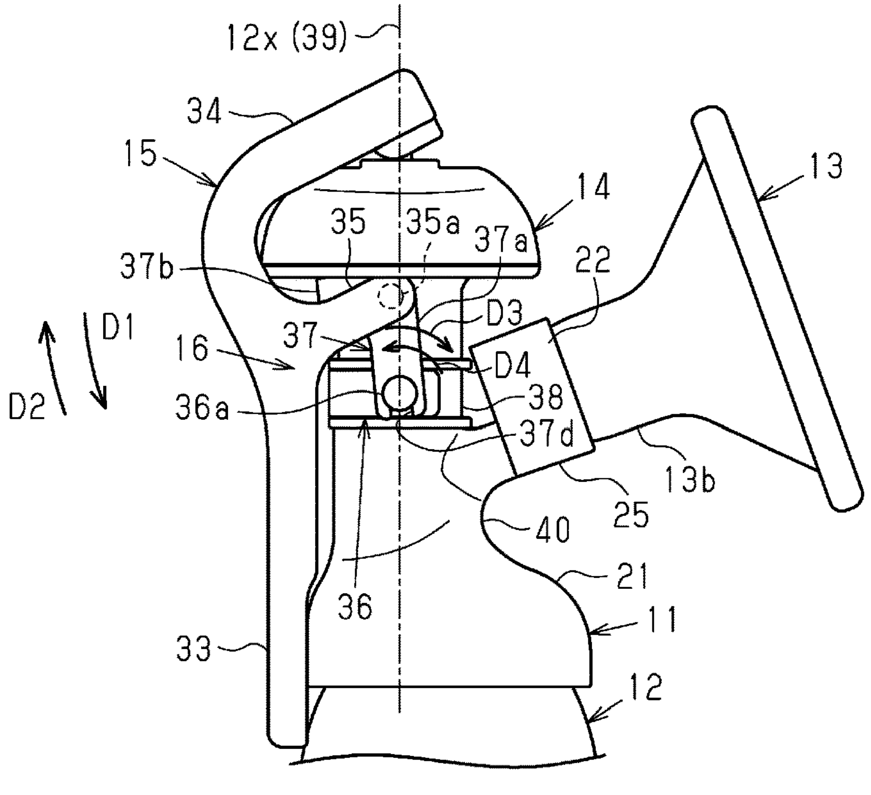
FIG. 6 is a side view showing the link mechanism when the inner passage of the breast pump of FIG. 1 is in the negative pressure state.

As shown in FIGS. 5 and 6, when the lever 33 is manually operated toward the side surface of the bottle 12 in the direction of arrow D1, the handle 15 lifts the diaphragm 14 with the lifting member 17. Specifically, when the user inputs operation force to the handle 15, the link member 37 is pushed by the handle pins 35*a*, and the connection portion 37*b* of the link member 37 is pivoted about the support pins 36*a* toward the body 11 in the direction of arrow D3. The operation force of the user required to move the handle 15 in the direction of arrow D1 gradually increases from when the operation starts. After moving beyond a given position during the operation, the operation force gradually decreases until reaching the maximum operation position of the handle 15. As the user operates the handle 15, the force applied by the handle 15 to the diaphragm 14 to lift the diaphragm 14 (output of handle 15 that lifts diaphragm 14) gradually increases as the diaphragm 14 rises and becomes the greatest at the maximum operation position of the handle 15.

As a result, the pressure of the inner passage 23 becomes negative and the extracted breast milk flows into the temporary reservoir 26 from the inlet path 25. Under the negative pressure state, the valve member 28 closes the bottom of the temporary reservoir 26. Thus, the breast milk the inlet path 25 is collected in the temporary reservoir 26.

As the user weakens the gripping force, the resilience of the diaphragm 14 pivots the handle 15 in the direction of arrow D2 and returns the inner passage 23 to normal pressure. This opens the valve member 28 of the temporary reservoir 26, and the breast milk flows into the bottle 12. In this case, the link member 37 is pivoted about the support pins 36*a* away from the body 11 in the direction of arrow D4. The handle 15 is repeatedly moved back and forth to extract breast milk. In this case, the inserted portion 30 is also moved back and forth in the negative pressure generating path 27. The inserted portion 30 moves in the negative pressure generating path 27 along the bottle axis 12*x*. Thus, the vertical movement of the inserted portion 30 is smooth.

Figure 7:
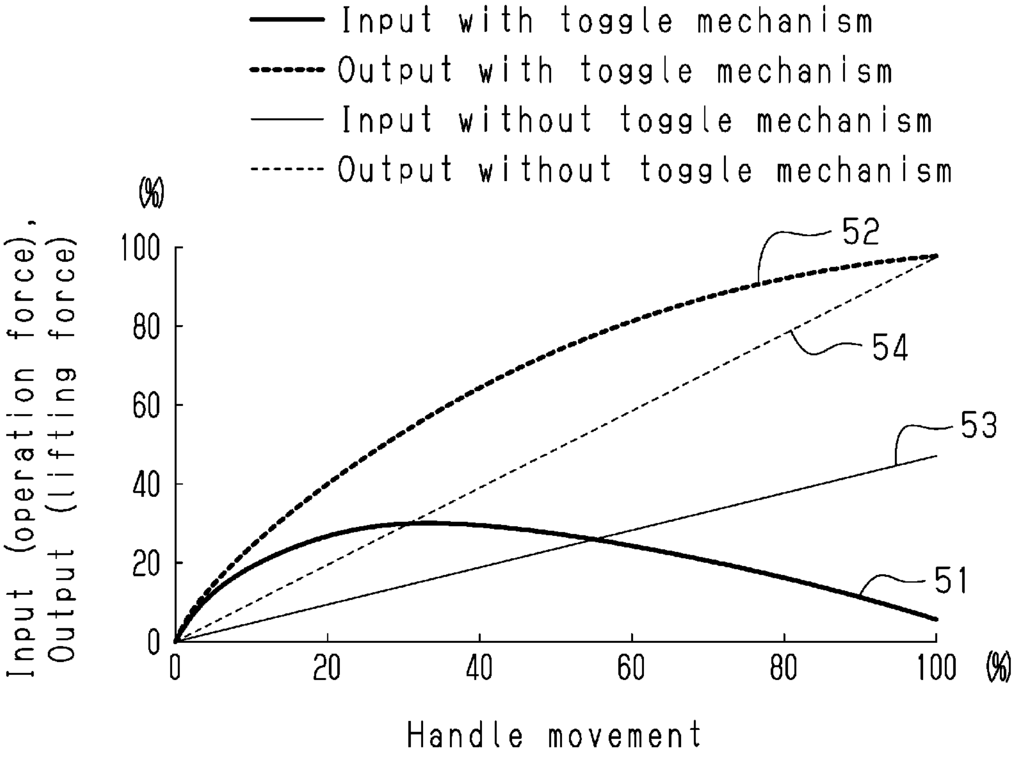
FIG. 7 is a characteristic diagram showing the relationship between the movement amount of a handle and the input/output of the handle.

A breast pump may be used to stimulate the nipple and breast by continuing the state of negative pressure for a predetermined period. When used in such a manner, the user operates and moves the handle 15 in the operation direction to the maximum movement position or to a location near the maximum movement position and maintains such a state for a predetermined period. As shown in FIG. 7, when a breast pump includes the toggle mechanism, the operation force input by the user to the handle 15 gradually increases from when the operation of the handle 15 starts until the handle 15 moves beyond a given position (changing point) during the operation. The operation force gradually decreases beyond the given position (refer to line 51). The output that lifts the diaphragm 14 (lifting force) becomes the greatest at the maximum operation position thereby ensuring lifting of the diaphragm 14 (refer to line 52). In contrast, when a breast pump does not include the toggle mechanism, the operation force, which is input by the user to the handle 15, and the lifting force, which is the output of the handle 15 that lifts the diaphragm 14, both gradually increase until reaching the maximum operation position (refer to line 53). Even when the breast pump does not include the toggle mechanism, the output of the handle 15 (lifting force) that lifts the diaphragm 14 becomes the greatest at the maximum operation position (refer to line 54).

Thus, the user of the breast pump 1 including the toggle mechanism uses less operation force to pivot the handle in the pivotal operation direction to the maximum pivot position or to a location near the maximum pivot position and can maintain such a state for a predetermined period so that the nipple and the breast can be stimulated with negative pressure.

The breast pump 1 described above has the following advantages.

(1) The link mechanism 16 reduces the input to the handle, or the operation force of the user, when the handle is moved to the maximum movement position or to a location near the maximum movement position. This reduces the muscle load on the hand or arm of the user.

(2) The output when the handle is moved to the maximum movement position or to a location near the maximum movement position, or the force that lifts the diaphragm 14, is equal to that when the toggle mechanism is not used.

(3) A simple toggle mechanism formed by the support member 36 and the link member 37 is implemented as the link mechanism 16 between the body 11 and the handle 15.

(4) The handle 15 is pivoted about the connection projection 32 relative to the body 11 with the support member 36 guided by the guide portion 38. Accordingly, the user can position the handle 15 relative to the body 11 to allow for easy operation.

(5) Even when enlarging the negative pressure generating path 27 to facilitate cleaning, the inserted portion 30 will still be inserted into the enlarged portion of the negative pressure generating path 27. This limits increases in the volume of the negative pressure generating path 27 and minimizes decreases in the milk extracting efficiency.

(6) The diaphragm 14 is lifted such that the inserted portion 30 is moved along the negative pressure generating path 27. The inserted portion 30 moves smoothly in the vertical direction and does not obstruct movement of the handle 15.

The above-described embodiment may be modified as follows.

The central axis of the negative pressure generating path 27 may be inclined toward, for example, the handle 15 relative to the bottle axis 12*x*.

The lifting member 17 may be omitted, and the connection projection 32 serving as a connector that is engaged with the engagement hole 34*b* of the handle 15 may be arranged on the outer surface of the diaphragm 14. In this case, the inserted portion 30 may be omitted or fixed to the inner surface of the diaphragm 14 by an adhesive or the like.

The inserted portion 30 may be separate from the lifting member 17. Specifically, the lifting member 17 may be formed by the plate 31 and the connection projection 32, and the inserted portion 30, which is a separate member, may be fixed to the plate 31 by an adhesive or swaging.

The inserted portion 30 may be spaced apart from the diaphragm 14. In one example, the inserted portion 30 is connected by a spacer that keeps the distance to the plate 31 fixed. In one example, the spacer is formed by one or more linear members or a shaft member to connect the inserted portion 30 and the plate 31.

The distal end surface of the inserted portion 30 is not particularly limited in shape and may be convex, flat, concave, or the like.

The outer circumferential surface of the inserted portion 30 is not particularly limited in shape as long as the volume of the negative pressure generating path 27 can be reduced and may have a wavy shape, a recessed shape, a projecting shape, or the like in side view.

The projection of the inserted portion 30 does not need to be shaped in conformance with the inner shape of the negative pressure generating path 27 into which the inserted portion 30 is inserted. For example, the inserted portion 30 may be shaped as a polygonal projection (outer shape) such as a triangular prism, a quadrangular prism, or a hexagonal column when the negative pressure generating path 27 includes a hollow and tubular internal space. Alternatively, the inserted portion 30 may be shaped as a cylindrical or tubular projection when the negative pressure generating path 27 has a polygonal inner shape such as that of a triangular prism, a quadrangular prism, or a hexagonal column.

The inserted portion 30 may be omitted from the lifting member 17. In this case, the negative pressure generating path 27 is narrowed to reduce the volume of the inner passage 23. This simplifies the structure of the lifting member 17.

In the above embodiment, the support member 36 of the link mechanism 16 is rotated along the guide portion 38, and the handle 15 is rotatable about the connection projection 32 relative to the body 11. However, the handle 15 does not need to be rotatable relative to the body 11. In this case, for example, the guide portion 38 of the attachment end 24 may be omitted and the support member 36 may be fixed to the body 11 in a non-rotatable manner. Alternatively, the support member 36 may be omitted, and the support pins 36*a*, which are engaged with the bearings 37*d* of the link mechanism 16, may be arranged directly on the body 11. When the support pins 36*a* are arranged directly on the body 11, the parts of the link mechanism 16 will be reduced in number.

When the handle 15 is arranged at the maximum operation position in the direction of arrow D1, the handle pins 35*a* may be positioned on either side of the straight line 39 that connects the point of action, which is where the connection projection 32 is engaged with the engagement hole 34*b*, to the support pins 36*a*. The movement amount of the handle pins 35*a* is in accordance with the length of the arms 37*a* or the like. The movement amount of the handle pins 35*a* may be set, for example, in accordance with the lift amount of the diaphragm 14.

In the above embodiment, the first pivotal fulcrum is where the pin holes 37*c* of the link member 37 are engaged with the handle pins 35*a* of the link piece 35. Alternatively, the first pivotal fulcrum may be where the pin holes 37*c* of the link piece 35 are engaged with the handle pins 35*a* of the link member 37.

In the above embodiment, the second pivotal fulcrum is where the bearings 37*d* of the link member 37 are engaged with the support pins 36*a* of the support member 36. Alternatively, the second pivotal fulcrum may be where the bearings 37*d* of the support member 36 are engaged with the support pins 36*a* of the link member 37.

The structure of the inner passage 23 is not particularly limited. The temporary reservoir 26 may be omitted. In this case, the valve member 28 may be omitted.

The specific structure of the link mechanism 16 is not particularly limited as long as the link mechanism 16 maximizes the operation force of the user applied to the handle 15 during a movement operation where the user moves the handle 15 in the operation direction to change the pressure of the inner passage 23 from normal to negative. The specific structure of the toggle mechanism is not particularly limited. For example, more than one link member 37 may be arranged between the body 11 and the handle 15.

The handle 15 does not need to extend downward toward the bottle 12 and may extend toward the user where the hood 13 is located. In this case, the user can pivot the handle 15 in a position of supination in which the palm is directed upward.

The bottle 12 does not need to be removable from the bottle attachment portion 21. and may be integrated with the bottle attachment portion 21. The hood 13 does not need to be removable from the hood attachment portion 22 and may be integrated with the hood attachment portion 22.

REFERENCE SIGNS LIST

1 . . . breast pump, 11 . . . body, 12 . . . bottle, 12*a* . . . bottle opening portion, 12*b* . . . male thread, 12*x* . . . bottle axis,

13 . . . hood, 13*a* . . . increased diameter portion, 13*b* . . . tubular portion, 13*c* . . . milking port, 14 . . . diaphragm, 14*a* . . . through-hole, 15 . . . handle, 16 . . . link mechanism, 17 . . . lifting member, 21 . . . bottle attachment portion, 21*a* . . . female thread, 22 . . . hood attachment portion, 23 . . . inner passage, 24 . . . attachment end, 25 . . . inlet path, 25*x* . . . center line, 26 . . . temporary reservoir, 27 . . . negative pressure generating path, 28 . . . valve member, 30 . . . inserted portion, 30*a* . . . gap, 31 . . . plate, 32 . . . connection projection, 32*a* . . . engagement groove, 33 . . . lever, 34 . . . attachment, 34*a* . . . recess, 34*b* . . . engagement hole, 35 . . . link piece, 35*a* . . . handle pin, 36 . . . support member, 36*a* . . . support pin, 37 . . . link member, 37*a* . . . arm, 37*b* . . . connection portion, 37*c* . . . pin hole, 37*d* . . . bearing, 38 . . . guide portion, 39 . . . straight line, 40 . . . neck

The invention claimed is:

1. A breast pump, comprising:

a body including:

a hood attachment portion to which a hood that is configured to be fitted to a breast and includes a milking port is attached;

a bottle attachment portion to which a bottle that stores breast milk is attached; and an inner passage extending between the hood attachment portion and the bottle attachment portion;

a diaphragm configured to generate negative pressure in the inner passage;

a handle manually operated to move back and forth or in a lateral direction toward and away from the bottle, the handle being configured to change a pressure of the inner passage from a normal state to a negative state by displacing the diaphragm in a lifting or a vertical direction away from the bottle; and a link mechanism configured to support the handle in a manner movable back and forth or in the lateral direction toward and away relative to the body, wherein the link mechanism is configured to apply an operation force to the handle that becomes maximal during handle movement when the handle is moved in an operation direction that changes the pressure from the normal state to the negative state, wherein:

the link mechanism includes a link member located between the handle and the body, the link member including a proximal end configured to be pivoted relative to the handle and a distal end configured to be pivoted relative to the body;

the link mechanism is configured so that when the handle is moved in the operation direction, a first pivotal fulcrum between the link member and the handle moves toward a straight line that connects a second pivotal fulcrum, between the link member and the body, and a point of action, at which the handle lifts the diaphragm; and when the handle is not operated, the straight line that connects the second pivotal fulcrum and the point of action coincides with a bottle axis in a side view, wherein:

the bottle axis extends parallel to a central axis of the bottle extending in a height direction of the bottle, and the side view is a view showing one of two second pivotal fulcrums positioned symmetrically with respect to the bottle axis.

2. The breast pump according to claim 1 wherein the link mechanism further includes:

a support member attached to the body in a manner rotatable in a circumferential direction, wherein the link member is attached to the body by the support member, and wherein the handle is rotatable about the point of action in the circumferential direction of the body.

3. The breast pump according to claim 2, wherein the link member further includes:

a first arm and a second arm, wherein the first arm and the second arm each include a proximal end and distal end, wherein the distal end of the first arm and the distal end of the second arm are each connected to the support member; and a connection portion connecting proximal end of the first arm and the proximal end of the second arm;

wherein the handle includes:

a lever, an attachment extending from a distal end of the lever and connected to the diaphragm to lift the diaphragm; and a first link piece and a second link piece extending from the lever and connected to the proximal ends of the first arm and the second arm;

and wherein the first pivotal fulcrum is a pin arranged on one of the first arm or the second arm and the link piece and is configured to be engaged with a pin hole arranged in the other one of the first arm or the second arm and the link piece, and wherein the second pivotal fulcrum is a support pin arranged on one of the first arm or the second arm and the support member and configured to be engaged with a bearing arranged on the other one of the first arm or the second arm and the support member.

4. The breast pump according to claim 1, further comprising:

an inserted portion inserted into the inner passage.

5. The breast pump according to claim 1, further comprising:

an inserted portion inserted into the inner passage, wherein the inner passage includes a negative pressure generating path closed by the diaphragm, the negative pressure generating path being arranged such that a central axis of the negative pressure generating path coincides with a bottle axis that extends parallel to a central axis of the bottle extending in a height direction of the bottle, wherein the inserted portion is inserted into the negative pressure generating path, and wherein the second pivotal fulcrum and the point of action are located on the bottle axis.

6. A breast pump, comprising:

a body;

a diaphragm;

a handle; and a link mechanism, wherein the body includes:

a hood attachment portion to which a hood configurable to be fitted to a breast and includes a milking port is attached;

a bottle attachment portion to which a bottle that stores breast milk is attached; and an inner passage extending between the hood attachment portion and the bottle attachment portion; and wherein the diaphragm is configured to generate negative pressure in the inner passage;

the handle is configurable to be manually operated to move back and forth or in a lateral direction toward and away from the bottle and configured to change a pressure of the inner passage from a normal state to a negative state by displacing the diaphragm in a lifting or a vertical direction away from the bottle;

the link mechanism is configured to support the handle as the handle moves back and forth or in the lateral direction toward and away relative to the body;

the link mechanism is further configured to apply an operation force to the handle that becomes maximal during movement of the handle in an operation direction that changes the pressure from the normal state to the negative state;

the link mechanism includes a link member located between the handle and the body, the link member including a proximal end configured to be pivoted relative to the handle and a distal end configured to be pivoted relative to the body;

the link mechanism is configured so that when the handle is moved in the operation direction, a first pivotal fulcrum between the link member and the handle moves toward a straight line that connects a second pivotal fulcrum, between the link member and the body, and a point of action, at which the handle lifts the diaphragm; and when the handle is not operated, the straight line that connects the second pivotal fulcrum and the point of action coincides with a bottle axis in a side view, wherein:

the bottle axis extends parallel to a central axis of the bottle extending in a height direction of the bottle; and the side view is a view showing one of two second pivotal fulcrums positioned symmetrically with respect to the bottle axis.

7. The breast pump of claim 6, wherein the link member includes:

a proximal end configured to be pivoted relative to the handle and a distal end configured to be pivoted relative to the body, and wherein the link mechanism is configured so that when the handle is moved in the operation direction, a first pivotal fulcrum between the link member and the handle moves toward a straight line that connects a second pivotal fulcrum, between the link member and the body, and a point of action, at which the handle lifts the diaphragm.

8. The breast pump of claim 7, further comprising:

an inserted portion inserted into the inner passage, wherein the inner passage includes a negative pressure generating path closed by the diaphragm, the negative pressure generating path being arranged such that a central axis of the negative pressure generating path coincides with a bottle axis that extends parallel to a central axis of the bottle extending in a height direction of the bottle, wherein the inserted portion is inserted into the negative pressure generating path, and wherein the second pivotal fulcrum and the point of action are located on the bottle axis.

9. The breast pump of claim 7, wherein the link member further includes:

a support member attached to the body in a manner rotatable in a circumferential direction, wherein the link member is attached to the body by the support member, and wherein the handle is rotatable about the point of action in the circumferential direction of the body.

10. The breast pump of claim 9, wherein the link member further includes:

a first arm and a second arm, wherein the first arm and the second arm each include a proximal end and distal end, wherein the distal end of the first arm and the distal end of the second arm are each connected to the support member; and a connection portion connecting proximal end of the first arm and the proximal end of the second arm.

11. The breast pump of claim 10, wherein the handle includes:

a lever, an attachment extending from a distal end of the lever and connected to the diaphragm to lift the diaphragm; and a first link piece and a second link piece extending from the lever and connected to the proximal ends of the first arm and the second arm;

wherein the first pivotal fulcrum is a pin arranged on one of the first arm or the second arm and the link piece and is configured to be engaged with a pin hole arranged in the other one of the first arm or the second arm and the link piece, and wherein the second pivotal fulcrum is a support pin arranged on one of the first arm or the second arm and the support member and configured to be engaged with a bearing arranged on the other one of the first arm or the second arm and the support member.

12. The breast pump of claim 6, further comprising:

an inserted portion inserted into the inner passage.

13. A breast pump, comprising:

a body;

a diaphragm;

a handle; and a link mechanism, wherein the body includes:

a hood attachment portion to which a hood configurable to be fitted to a breast and includes a milking port is attached;

a bottle attachment portion to which a bottle that stores breast milk is attached; and an inner passage extending between the hood attachment portion and the bottle attachment portion; and wherein:

the diaphragm is configured to generate negative pressure in the inner passage;

the handle is configurable to be manually operated to move back and forth or in a lateral direction toward and away from the bottle and configured to change a pressure of the inner passage from a normal state to a negative state by displacing the diaphragm in a lifting or a vertical direction away from the bottle;

the link mechanism is configured to support the handle as the handle moves back and forth or in a the lateral direction toward and away relative to the body;

the link mechanism is further configured to apply an operation force to the handle that becomes maximal during movement of the handle in an operation direction that changes the pressure from the normal state to the negative state;

the link mechanism includes a link member located between the handle and the body, the link member including a proximal end configured to be pivoted relative to the handle and a distal end configured to be pivoted relative to the body;

the link mechanism is configured so that when the handle is moved in the operation direction, a first pivotal fulcrum between the link member and the handle moves toward a straight line that connects a second pivotal fulcrum, between the link member and the body, and a point of action, at which the handle lifts the diaphragm;

when the handle is not operated, the straight line that connects the second pivotal fulcrum and the point of action coincides with a bottle axis in a side view, wherein:

the bottle axis extends parallel to a central axis of the bottle extending in a height direction of the bottle; and the side view is a view showing one of two second pivotal fulcrums positioned symmetrically with respect to the bottle axis; and wherein the link member includes:

a proximal end configured to be pivoted relative to the handle and a distal end configured to be pivoted relative to the body.

14. The breast pump of claim 13, further comprising:

an inserted portion inserted into the inner passage, wherein the inner passage includes a negative pressure generating path closed by the diaphragm, the negative pressure generating path being arranged such that a central axis of the negative pressure generating path coincides with a bottle axis that extends parallel to a central axis of the bottle extending in a height direction of the bottle, wherein the inserted portion is inserted into the negative pressure generating path, and wherein the second pivotal fulcrum and the point of action are located on the bottle axis.

15. The breast pump of claim 13, wherein the link member further includes:

a support member attached to the body in a manner rotatable in a circumferential direction, wherein the link member is attached to the body by the support member, and wherein the handle is rotatable about the point of action in the circumferential direction of the body.

16. The breast pump of claim 15, wherein the link member further includes:

a first arm and a second arm, wherein the first arm and the second arm each include a proximal end and distal end, wherein the distal end of the first arm and the distal end of the second arm are each connected to the support member; and a connection portion connecting proximal end of the first arm and the proximal end of the second arm.

17. The breast pump of claim 16, wherein the handle includes:

a lever;

an attachment extending from a distal end of the lever and connected to the diaphragm to lift the diaphragm; and a first link piece and a second link piece extending from the lever and connected to the proximal ends of the first arm and the second arm;

wherein the first pivotal fulcrum is a pin arranged on one of the first arm or the second arm and the link piece and is configured to be engaged with a pin hole arranged in the other one of the first arm or the second arm and the link piece, and wherein the second pivotal fulcrum is a support pin arranged on one of the first arm or the second arm and the support member and configured to be engaged with a bearing arranged on the other one of the first arm or the second arm and the support member.

18. The breast pump of claim 13, further comprising:

an inserted portion inserted into the inner passage.

* * * * *